(12) United States Patent
Ruskin

(10) Patent No.: US 8,689,484 B2
(45) Date of Patent: Apr. 8, 2014

(54) WEED CONTROL AND ROOT BARRIER

(76) Inventor: Rodney Ruskin, San Rafael, CA (US)

( * ) Notice: Subject to any disclaimer, the term of this patent is extended or adjusted under 35 U.S.C. 154(b) by 568 days.

(21) Appl. No.: 13/099,645

(22) Filed: May 3, 2011

(65) Prior Publication Data

US 2011/0289834 A1    Dec. 1, 2011

Related U.S. Application Data

(60) Provisional application No. 61/349,803, filed on May 28, 2010.

(51) Int. Cl.
*A01N 33/18*    (2006.01)

(52) U.S. Cl.
USPC .......................................................... 47/32.7

(58) Field of Classification Search
USPC .......................................................... 47/32.7
See application file for complete search history.

(56) References Cited

U.S. PATENT DOCUMENTS

| | | | |
|---|---|---|---|
| 5,116,414 A | 5/1992 | Burton et al. | |
| 5,181,952 A | 1/1993 | Burton et al. | |
| 5,575,112 A * | 11/1996 | Scheubel | 47/78 |
| 6,095,785 A | 8/2000 | Kudert et al. | |
| 6,224,957 B1 | 5/2001 | Crook et al. | |
| 6,803,051 B1 | 10/2004 | Voris et al. | |
| 6,821,928 B2 | 11/2004 | Ruskin | |
| 7,012,042 B1 | 3/2006 | Cataldo et al. | |
| 7,335,374 B2 | 2/2008 | Voris et al. | |
| 7,465,390 B2 | 12/2008 | Potts | |
| 2002/0192259 A1* | 12/2002 | Voris et al. | 424/411 |
| 2004/0266625 A1 | 12/2004 | Lipinsky et al. | |

(Continued)

FOREIGN PATENT DOCUMENTS

| | | |
|---|---|---|
| EP | 0 307 720 A2 | 3/1989 |
| EP | 307720 A2 * | 3/1989 |
| WO | WO 97/47190 | 12/1997 |
| WO | WO 02/43487 A2 | 6/2002 |

OTHER PUBLICATIONS

PCT International Search Report and Written Opinion of the International Searching Authority, dated Jul. 20, 2012 issued in the corresponding PCT Application No. PCT/US2011/037548, 15 pages.

(Continued)

*Primary Examiner* — Frank T Palo
(74) *Attorney, Agent, or Firm* — Christie, Parker & Hale, LLP

(57) ABSTRACT

A polyolefin sheet material carries layered segments of a polymer which contains a herbicide such as a 2,6-dinitroaniline. The sheet material can be porous to permit free passage of water. It may be either a perforated sheet or a woven or non-woven material. A desired material is a non-woven fabric of non-biodegradable polyolefin material, such as a geotextile, for example. In order to obtain a root growth-repelling property, the herbicide is blended with a polymer which is attached or bonded to or embedded in the geotextile, or other polyolefin carrier sheet material, in the form of spaced apart layered segments. Diffusion of the herbicide directly into the soil is prevented by a barrier material positioned on, coated on, or otherwise bonded to the layered segments, to encompass surfaces of the segments which are otherwise exposed on the sheet material. Essentially all of the herbicide contained in the layered segments is directed into the soil virtually exclusively by means of its long term migration through the carrier sheet material.

23 Claims, 6 Drawing Sheets

(56) References Cited

U.S. PATENT DOCUMENTS

2009/0242492 A1 10/2009 Ruskin
2011/0289834 A1* 12/2011 Ruskin ........................... 47/32.7
2013/0192132 A1* 8/2013 Ruskin ........................... 47/32.8

OTHER PUBLICATIONS

PCT International Search Report dated Feb. 21, 2012 for corresponding PCT Application No. PCT/US2011/037548, 4 pages.

PCT International Search Report and the Written Opinion of the International Searching Authority, dated Apr. 10, 2012 issued in the corresponding PCT Application No. PCT/US2011/037548, 15 pages.

Typar Biobarrier; Guaranteed Protection Against Root Damage (brochure); 2009; Tennessee, USA; 6 Pages.

* cited by examiner

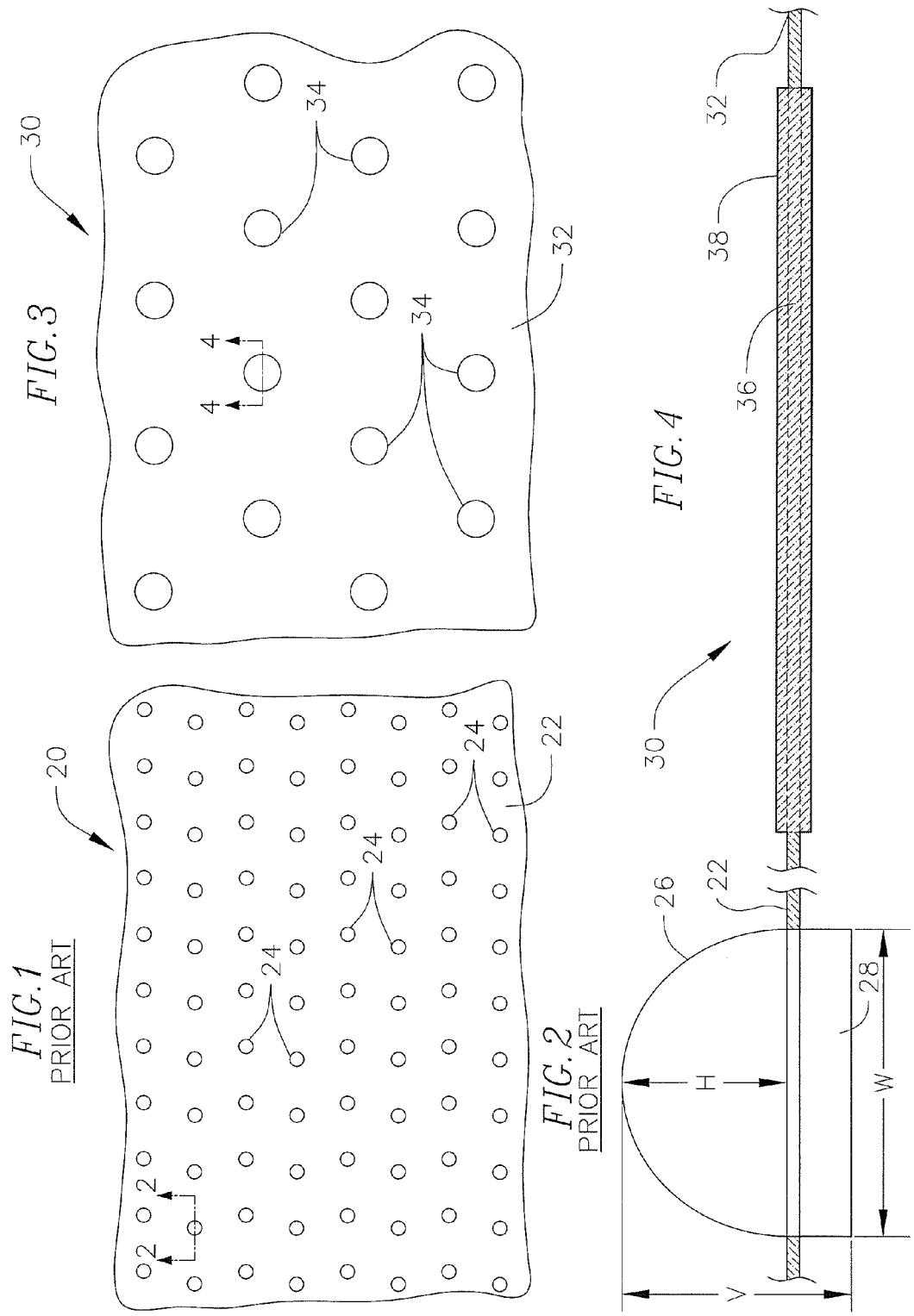

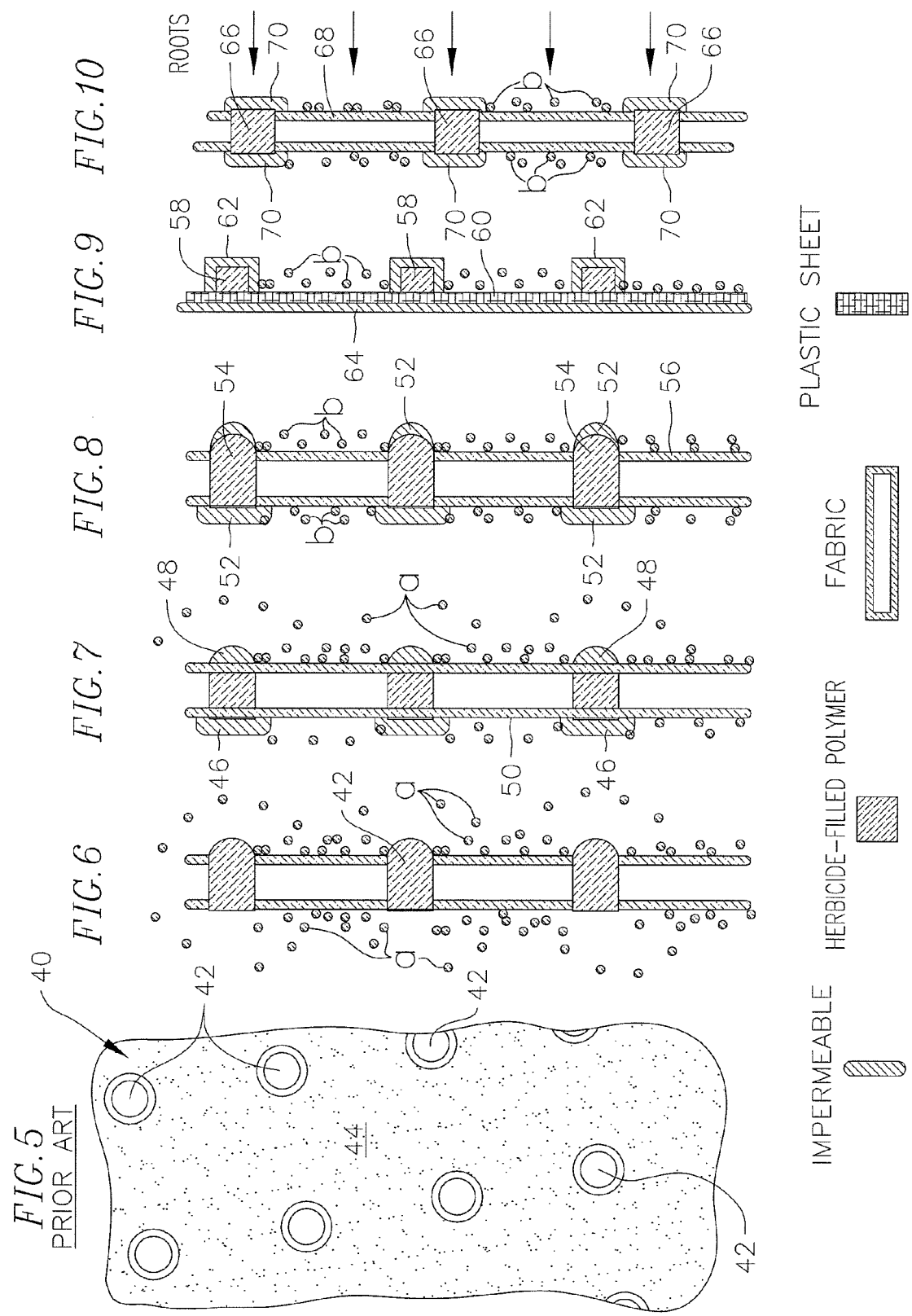

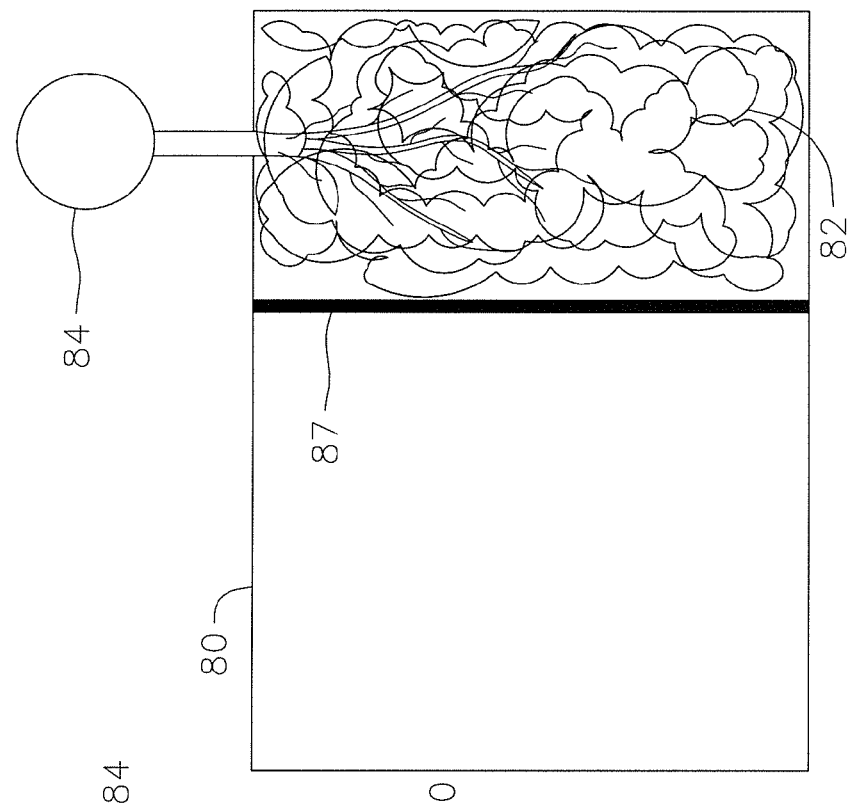
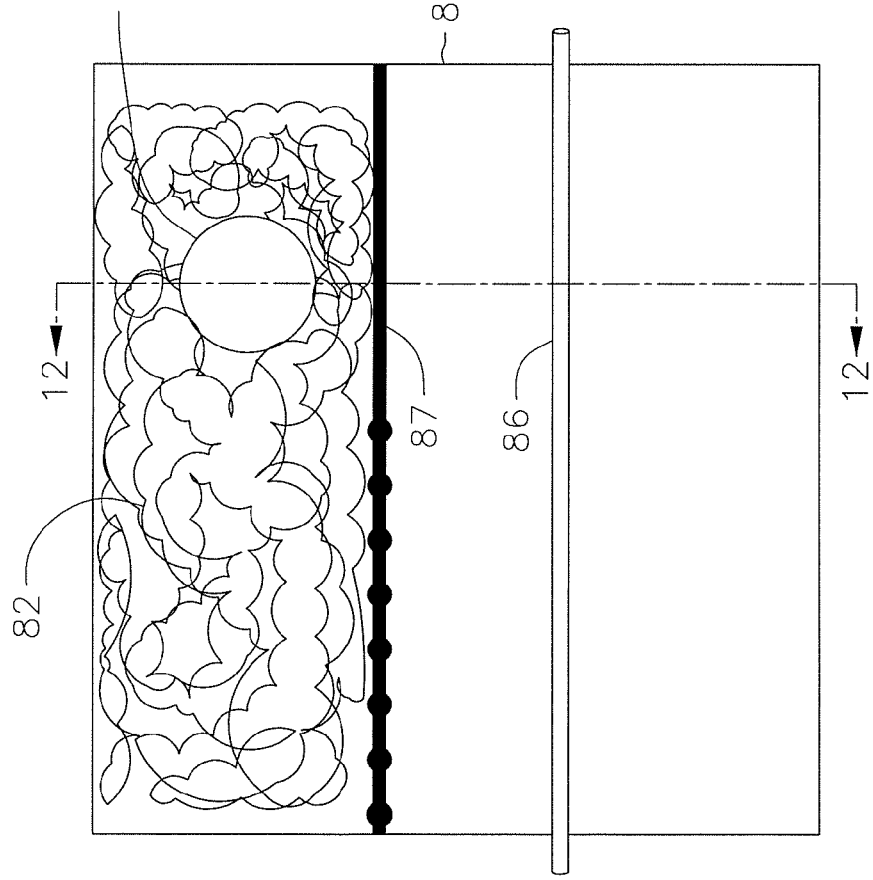

WEED CONTROL AND ROOT BARRIER

CROSS-REFERENCE TO RELATED APPLICATION

This application claims priority to U.S. Provisional Application No. 61/349,803, filed May 28, 2010, which is fully incorporated herein by this reference.

FIELD OF THE INVENTION

This invention relates generally to products used for root barriers and/or weed control; and more particularly, to flexible sheet materials that function as carriers for spaced apart layers of root growth-inhibiting material attached to and distributed across the face of the sheet material. These products, when placed in the ground, slowly release the root growth-inhibiting material at a release rate that provides continuous long term protection against undesired root growth.

BACKGROUND

Original work done by Battelle (Battelle Memorial Institute) in the 1970s was directed to keeping root growth out of nuclear waste burial sites for a minimum expected life of 100 years. Battelle addressed the problem by developing buried pellets containing a herbicide (2,6-dinitroaniline) incorporated into a polymer (polyethylene) along with carbon black. The Battelle buried pellets, approximately 9 mm in diameter, were placed directly into the soil on a grid pattern at 2.5 to 5.0 cm spacing.

The work done by Battelle later resulted in issuance of U.S. Pat. Nos. 5,116,414 and 5,181,952 to Burton et al. Both of these patents disclose porous sheet materials having spaced apart bodies of a polymer containing 2,6 dinitroaniline for use as a root growth-inhibiting product; and both patents are incorporated in their entirety herein by this reference.

In the 1980s, Battelle's idea was followed by a development of geotextiles, particularly a non-woven fabric used as a carrier for pellets containing a herbicide. Pellets containing the herbicide trifluralin are spaced apart across the surface of the fabric, and when the fabric is buried in the ground, it affords protection against undesired root growth. One development which has been in use for many years is the geotextile fabric supplied by Fiberweb, Inc. which includes a pattern of nodules containing the herbicide trifluralin. That root barrier and weed control product is and has been sold under the registered mark Biobarrier, and is referred to herein as "the Biobarrier product."

In the Biobarrier product, the presence of the trifluralin prevents root tip cell division; and when the Biobarrier material is used as a root barrier or for weed control, for example, the root systems of the weeds do not grow in adjacent areas into which the herbicide is dispersed.

In the Biobarrier product the nodules containing trifluralin applied to the fabric generally have a hemispherical shape, from which the herbicide can radiate directly outward into the soil during use. In one embodiment, the nodules have a radial dimension of about 9 mm, with a mutual spacing of about 4 cm. Each nodule radiates out a protective spherical dimension of about 3 mm, so each protects a sphere volume of about 14 cu cm. Assuming an area of 1 sq m, with nodules at 4 cm spacing, there are 625 nodules/sq m, or a zone of protection of 8,750 cu cm formed by the trifluralin moving in overlapping spheres directly away from the nodules.

The present invention is based on a recognition that the amount of herbicide used in the Biobarrier product, or similar products, is excessive, in fact wasted, given the amount of herbicide actually needed to provide a practical level of protection. This invention provides a much more efficient use of the herbicide material. Assuming the same 1 sq. m area of the fabric, for instance, an effective narrow zone of protection having a volume of 1,000 cu cm or less can be produced along the fabric by the present invention. This avoids the otherwise undesired wasteful prior art use of the herbicide. Advantages of the present invention include longer life of the herbicide and/or lower product cost for the same level of protection. Other improvements are also provided, as described in more detail below.

SUMMARY OF THE INVENTION

Briefly, one embodiment of the present invention comprises a material for preventing entry of unwanted roots into a volume of soil. A flexible carrier sheet of a herbicide-absorbing material, such as a polyolefin material, includes discrete spaced-apart layered segments of a polymer containing a herbicide, such as a herbicidal dinitroaniline in a composition effective to retain and control the release rate of the dinitroaniline. The layered segments can contain a dispersed nanoclay to further control release rate. The layered segments also include a polymeric barrier film applied to the exposed surfaces of the segments. The barrier material blocks diffusion of the herbicide through the surfaces of the layered segments covered by the barrier film. When the carrier sheet material is buried in soil, diffusion of the dinitroaniline directly from the layered segments into the soil is prevented by the barrier. The dinitroaniline will diffuse first into the carrier sheet from the layered segments, and from there into the adjacent soil at such a rate, and over such a period of time, as to exclude roots over a period of years without killing plants beyond the seedling stage.

The barrier layers prevent direct movement of the herbicide out of the layered segments and into the soil, which forces essentially all of the herbicide contained in the layered segments to be directed laterally through the carrier sheet and dispersed therefrom at a controlled release rate. As a result, the long term effectiveness of the product can be increased greatly at a substantial cost savings.

These and other aspects of the invention will be more fully understood by referring to the following detailed description and the accompanying drawings.

BRIEF DESCRIPTION OF THE DRAWINGS

FIG. 1 is a semi-schematic illustration of a prior art geotextile sheet material containing spaced-apart nodules of a root growth-inhibiting material.

FIG. 2 is a cross-section taken on line 2-2 of FIG. 1 and depicting dimensions of the nodules characteristic of the prior art sheet material.

FIG. 3 is a semi-schematic illustration showing a geotextile sheet material with spaced apart layered segments having barrier properties according to principles of this invention.

FIG. 4 is a cross-section taken on line 4-4 of FIG. 3 and depicting dimensions of the layered segments according to the present invention.

In the accompanying drawings, FIGS. 5 through 10, the roots are depicted as approaching from the right hand side. The arc of dots marked "a" symbolizes the movement of the herbicide away from the layered segments, nodules or disks. The flat plane of dots marked "b" symbolizes movement of the herbicide away from the fabric.

FIG. 5 shows a prior art product. The original fabric is typically white, but the herbicide has migrated from the pellets carried by the fabric through the fabric, approximately equally on both sides, to discolor the fabric.

FIG. 6 shows a schematic cross-section of the prior art product with the dots symbolizing the movement of herbicide through the soil. The large circle of dots marked "a" symbolizes the movement of the herbicide away from the nodules contained in the prior art product.

FIG. 7 shows a schematic cross-section with a barrier molded on the back of a nodule. The dots symbolize the movement of herbicide through the soil, with the only movement on the protected side being movement from the fabric.

FIG. 8 shows a schematic cross-section with a barrier molded on both sides of the nodule. The dots symbolize the movement of herbicide through the soil, with the only movement on both sides being movement from the fabric.

FIG. 9 shows a disk-shaped layered segment molded to a non-porous plastic sheet with a barrier molded over the top of the disk. The sheet has a barrier layer so that no herbicide moves out from the rear side of the sheet.

FIG. 10 shows a disk-shaped layered segment molded through the fabric with a barrier applied to both sides of the disk.

FIG. 11 is a schematic cross-sectional plan view illustrating an experimental root growth-intrusion comparison between a prior art weed control and root barrier product and an improved product made according its principles of this invention.

FIG. 12 is a schematic cross-sectional side view taken on line 12-12 of FIG. 11.

Figure 13:
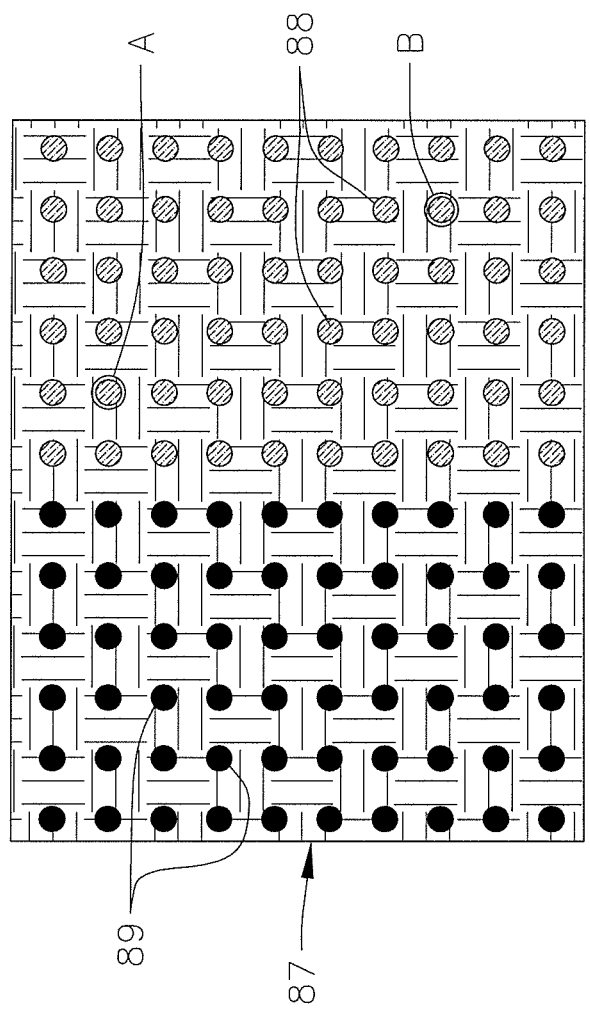

FIG. 13 is a schematic diagram illustrating a sheet of a root growth barrier fabric used in the comparative tests.

Figure 14:
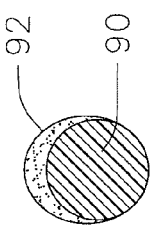

FIG. 14 is a cross-sectional view illustrating a co-extruded form of the layered segments of herbicide-containing material and their resinous barrier layers, according to one method for making the product of this invention.

Figure 15:
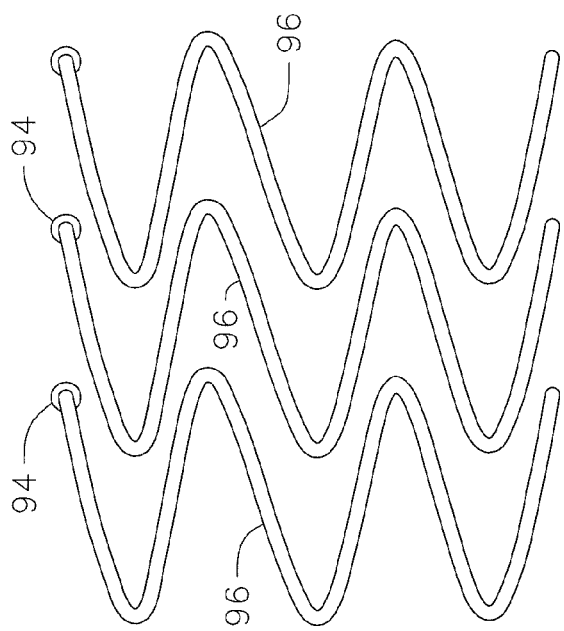

FIG. 15 is a schematic plan elevational view showing a pattern of co-extrusions produced by a co-extruder used in the process of FIG. 14.

Figure 16:
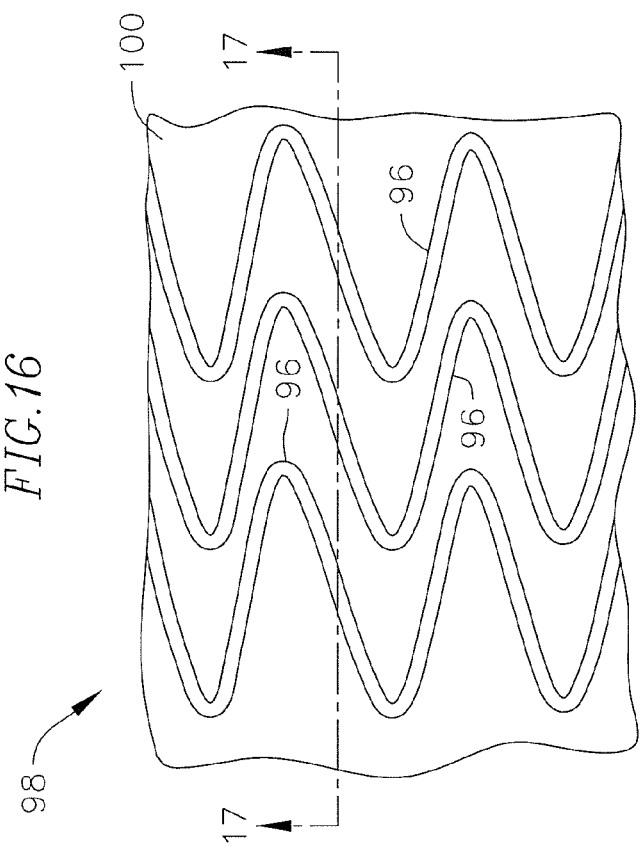

FIG. 16 is a fragmentary plan elevational view showing a finished geotextile fabric with the co-extruded pattern formed by the co-extruder of FIG. 15.

Figure 17:
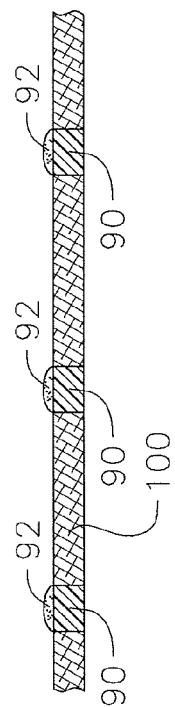

FIG. 17 is a cross-sectional view taken on line 17-17 of FIG. 16.

Figure 18:
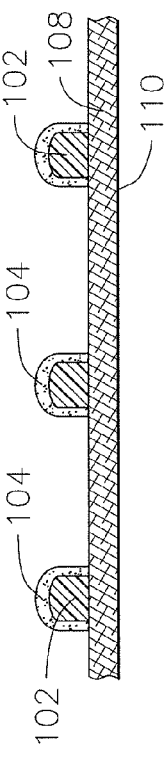

FIG. 18 is a cross-sectional view illustrating a co-extruded form of the layered segments of herbicide-containing material and their resinous barrier layers, according to another method for making an alternate embodiment of the invention.

Figure 19:
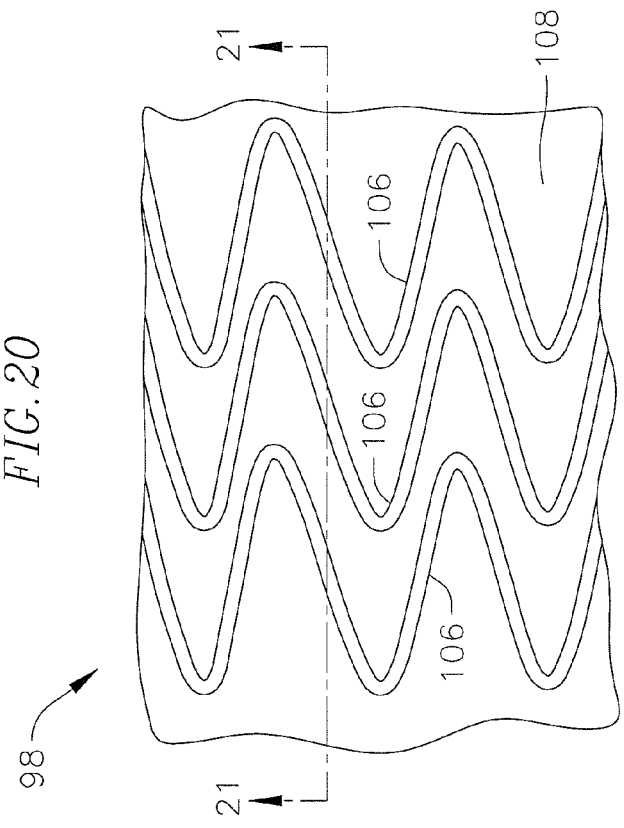

FIG. 19 is a schematic plan view showing a pattern of co-extrusions produced by a co-extruder used in the process of FIG. 18.

Figure 20:
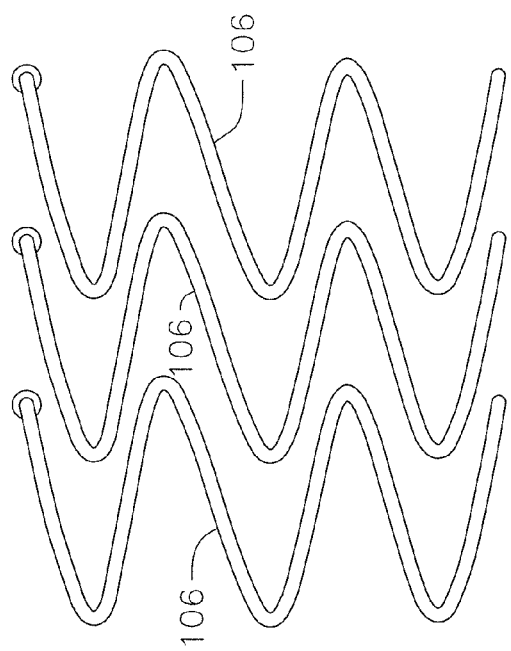

FIG. 20 is a fragmentary plan elevational view showing a non-porous fabric with a pattern of co-extrusions formed by the co-extruder of FIG. 19.

Figure 21:
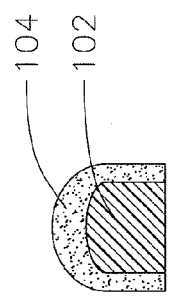

FIG. 21 is a cross-sectional view taken on line 21-21 of FIG. 20.

DETAILED DESCRIPTION

The invention is best understood by first referring to FIGS. 1 and 2, which illustrate a prior art root growth-inhibiting sheet 20. The sheet comprises a porous non-woven polyolefin geotextile fabric 22, with nodules 24 of a polyolefin molded both into and onto the fabric. The nodules are dispersed across the face of the sheet, preferably in a uniform rectangular or square grid pattern as shown in FIG. 1. The nodules 24 contain the herbicide trifluralin and carbon black dispersed in the polyolefin material. This product is sold under the registered mark Biobarrier. In use, the trifluralin is released directly from the nodules into the soil. The trifluralin is also absorbed by the polyolefin fabric and migrates through the fabric and then into the soil, away from the free surface areas of the fabric between the nodules.

FIG. 2 depicts the size and shape of the nodules of herbicide-containing material as applied to the prior art sheet 20. In the process of applying the nodules to the geotextile fabric sheet, the nodules are formed by molding techniques, and the hot molten material forming the nodules passes through the fabric and bonds the nodules to the sheet. The resulting nodules are formed in a generally hemispherical shape at 26 on one side of the sheet and in a smaller size at 28 on the reverse side of the sheet.

Measurement tests carried out on the prior art product shown in FIGS. 1 and 2 exhibited the following dimensions:

(1) In a 204 sq. inch (17-inch×12-inch) area, there are 88 of the spherical shaped nodules, with a horizontal and vertical spacing at about 1.2 inches between nodules.

(2) The fabric layer has a thickness of about 0.019-inch.

(3) The vertical height (v) of the nodules is about 0.31-inch, the height of the spherical shaped nodule (h) above the sheet is 0.21 inch, and its width (w) is 0.41-inch. Each nodule's volume is 0.0333 cu inch.

FIGS. 3 and 4 illustrate a weed control and root barrier sheet 30 according to principles of this invention. The sheet 30 comprises a thin, flexible, non-biodegradable carrier 32 which can comprise a porous non-woven polyolefin geotextile fabric similar to that described previously; or the carrier can comprise a thin, flexible plain non-porous sheet made of a non-biodegradable plastic material, such as a polyolefin, as described below.

Referring to the embodiment shown in FIG. 3, a pattern of mutually spaced-apart layered segments 34 of a herbicide-containing material are attached to a surface of the carrier sheet. The layered segments 34 are uniformly spaced-apart horizontally and vertically across the face of the sheet, in a pattern which can be a uniform grid pattern, or a pattern with offset rows as shown in FIG. 3. The surface area of the segments 34 is substantially larger than the projected surface areas of the nodules 24 in the prior art FIG. 1 embodiment. The segments 34 are also substantially thinner, and the individual number of segments 34 per row is reduced considerably, compared to the prior art embodiment of FIG. 1.

The layered segments of herbicide material are attached to the carrier sheet in the form of generally flat disks 36 shown in FIG. 4. The disk-shaped elements are generally wider in diameter or width compared to their thickness. They are preferably applied to the carrier in flexible sheet form, by injection molding, extrusion, coating, or printing techniques. In the process of applying the segments, the hot molding or coating material passes through a porous carrier and can form a disk-shaped layer or film on both sides of the carrier, as well as being embedded in the carrier, as illustrated in FIG. 4. The process of applying the disk-shaped elements can vary, to produce segments which are permanently bonded to, coated on, or otherwise embedded in the carrier material. The embodiment of FIG. 3 shows the disk-shaped elements applied in a generally circular shape, although the shapes and patterns of the disks or other layered segments can vary, depending upon desired molding, extrusion, coating, or printing techniques.

Following the step of applying the layered segments to the carrier sheet, the exposed surfaces of the disk-shaped elements 36 or other layered segments are covered with a thin barrier film 38 as illustrated in FIG. 4. The exposed surfaces of the disk-shaped elements on both sides of the carrier sheet are covered by the barrier film. The barrier film, described in more detail below, can be applied to the disks by injection molding, extrusion, coating, printing, or paint coating techniques. The barrier film also can be applied simultaneously with the molding of the disks by means of co-injection molding. The objective is to cover virtually the entire exposed surfaces of the disks, to provide a barrier between direct exposure of the herbicide-containing disks or other layered segments, and the soil, during use.

The present invention can be carried out using other shapes and sizes of the herbicide-containing material. For instance, in one embodiment, nodules similar to the Biobarrier product could be used, along with the barrier layer of this invention. For reasons explained below, the barrier layers enable one to use layered segments of various shapes and sizes, but with a reduced volume that uses much less herbicide.

Measurement tests carried out on the embodiments of FIGS. 3 and 4 have the following dimensions:

(1) In a 204 sq. inch area, there are 16 of the disk-shaped elements, in a pattern that contains from about 11 to about 12 disks per sq. ft, compared to the FIG. 1 embodiment which contains about 64 nodules per sq. ft.

(2) The fabric layer has a thickness of about 0.019 inch.

(3) The disk has a diameter of 1.0 inch and a width of 0.038 inch and has a volume of 0.030 cu inch.

Comparatively speaking, the nodules 24 of the prior art sheet material have a greater volume-to-area ratio (more than 10 times greater) than the disk-shaped segments 34 of the present invention. In one embodiment of the invention, the volume-to-area ratio is less than 0.10 inch. (The volume-to-area ratio is the ratio of the volume of material contained in each layered segment or nodule versus the surface area of the fabric covered by the same segment or nodule. This ratio can be expressed in cu cm/sq cm, for example, and can be measured in terms of an average ratio for a specific area of the fabric.)

Referring more specifically to the present invention, the carrier sheet 32, in a preferred embodiment, comprises a thin, flexible porous polymeric carrier material, and more particularly, a non-woven geotextile fabric material described previously. The preferred composition of the carrier sheet is a polymeric material to which the layered segments can be bonded or embedded and which can absorb the herbicide that diffuses or migrates from contact with the layered segments. A presently preferred carrier material is a thermoplastic polyolefin such as polyethylene or polypropylene made into the non-woven fabric. The present invention is based in part on a recognition that such carrier materials absorb the diffused herbicide similar to a sponge or ink blotter, constantly absorbing the herbicide migrating from the layered disk elements into the carrier, and transmitting the absorbed herbicide laterally through the carrier, from which the herbicide is released into the soil at a desired continuous and controlled release rate.

In addition to thermoplastic polyolefin materials generally, the carrier sheet more specifically can be made from the group of materials consisting of polyethylenes, polypropylenes, copolymers and mixtures of polyethylenes and polypropylenes, polyvinylacetate, poly(ethylene vinyl acetate), poly(ethyleneacrylic acid), poly(ethylene ethyl acrylate), polybutylene.

In an alternate form of the invention, if transmission of water through the sheet is not required, the carrier sheet can comprise a plain non-porous non-biodegradable plastic sheet; and in one embodiment, the plastic sheet can be made from the previously described carrier sheet materials. The non-porous plastic sheet also can be coated with a barrier material (described below) on one side to block passage of herbicide from that side of the sheet.

The layered segments of herbicide-containing material can comprise any polymeric material in which the herbicide can be dispersed, which can be bonded to the carrier sheet, and from which the herbicide can migrate at a controlled rate. The herbicide material is preferably dispersed in a polymeric carrier material, preferably a thermoplastic polyolefin material, such as polyethylene. More specifically, the polymer contained in the layered segments is selected from the group consisting of polyethylenes, polypropylenes, copolymers and mixtures of polyethylenes and polypropylenes, polyvinylacetate, poly(ethylene vinyl acetate), poly(ethyleneacrylic acid), poly(ethylene ethyl acrylate), polybutylene.

The presently preferred herbicide material is a dinitroaniline. The common names and chemical identification of representative dinitroaniline compounds which can be used in the present invention are:

Trifluralin—N,N-di-n-propyl-4-trifluoromethyl 2,6-dinitroaniline, having the generic name trifluralin-2,6-dinitro-N,N-dipropyl-p-toluidine, Benfluralin—N-butyl-N-ethyl-2,6-dinitro-4(trifluoromethyl)benzenamine, Isopropalin—4-isopropyl-2,6-dinitro-N,N-dipropylaniline, Oryzalin—3,5-dinitro-N.sup.4,N.sup.4-dipropylsulfanilamide, Ethalfluralin—N-ethyl-.alpha.,.alpha.,.alpha.-trifluoro-N-(methylallyl)-2,6-dinitro-p-toluidine, Pendimethalin—N-(1-ethylpropyl)-2,6-dinitro-3,4-xylidine, Profluralin—N-(cyclopropylmethyl)-.alpha.,.alpha.,.alpha.-trifluoro-2,6-di nitro-N-propyl-p-toluidine.

In one embodiment of the invention, the formulation for the herbicide-containing material comprises a herbicide dispersed in a particulate material that absorbs the herbicide, such as carbon black or a nanoclay, for example. The herbicide-containing material is preferably made by a mixture of thermoplastic polyolefin, such as polyethylene, and a herbicide absorbed into carbon black and then dispersed into the polymeric carrier material. The amount of carbon black or other particulate herbicide-absorbing material in the formulation is sufficient to retain and control the release rate of the herbicide. In one embodiment, the herbicide-containing material comprises a polyolefin material containing a dispersed herbicidal dinitroaniline and carbon black in which the concentration of the herbicide is from about 2 wt. % to about 30 wt. %, based on the total solids contained in the herbicide-containing material. In another embodiment, the herbicide-containing material comprises 50% polyethylene, 25% trifluralin, and 25% carbon black. This herbicide-containing material is available under the mark ROOTGUARD® from Geoflow, Inc.

In one form of the invention, the herbicide-containing material can include a fine particulate filler material dispersed in an amount that reduces the diffusion rate of the herbicide from the polymer at a controlled, slow release rate. Such a fine particulate material can include a dispersion of a nanoclay; and more particularly, the slow release herbicide-containing material can be made by formulations and methods disclosed in U.S. Pat. No. 6,821,928 to Ruskin, which is incorporated herein by this reference.

The barrier material comprises any polymeric material which can be applied to the layered segments in thin-film form and which resists long term migration of the herbicide through the barrier, in the sense that migration of the herbicide is not slowed down, but virtually stopped. In use, the barrier will encompass the layered segments and essentially block diffusion of the herbicide directly into the soil from the disk-shaped elements which would otherwise be in direct contact with the soil. The barrier film causes essentially all of the herbicide from the layered segments to be absorbed into the carrier sheet, from which the herbicide can then be released at a controlled rate from areas of the sheet not covered by the layered segments of herbicide-containing material.

In one embodiment, the preferred barrier material is ethylene-vinyl alcohol random copolymer (EVOH), which can be applied as a paint coating, although any polymer that forms an impenetrable coating in dry thin-film form can be used. Polymers such as those used in forming paint film binders, or lacquers, including vinyls, polyolefins, polyurethanes, and acrylics, are examples. In another embodiment the barrier film can contain dispersed particles of a fine particulate filler material, such as a nanoclay, or other nano-particles. These compositions can produce barrier films that further resist or block diffusion of the herbicide through the applied barrier layers.

The present invention is adapted for various uses involving inhibition of root growth, particularly the exclusion of the roots from areas in which they are undesirable, e.g., waste burial sites, from underground pipelines, basements, hardscapes such as sidewalks, septic drain-fields, or simply the boundaries between adjacent properties. One use, in particular, can provide a root barrier to redirect roots in onsite sewage drain fields. As mentioned previously, the herbicide-containing layers may be formed of polymers, e.g., polyethylene, containing in admixture dinitroanilines, such as N,N-di-n-propyl-4-trifluoromethyl 2,6-dinitroaniline, having the generic name trifluralin. Referring to the prior art, during use the Biobarrier product releases trifluralin directly from the nodules into the soil. The trifluralin also is absorbed by the polyolefin fabric and moves through the fabric into the soil. Inhibiting movement of the trifluralin directly into the soil from the nodule (as with the present invention) can increase considerably the effective life of the product. EVOH and nanoclay compounds, for example, are effective barriers to the movement of dinitroanilines. This is achieved by the present invention when the barrier layers are placed immediately between the layered segments and the soil. The Biobarrier material releases trifluralin directly into the soil on both sides of the fabric. The trifluralin moves in overlapping spheres away from each nodule, which is unnecessary and wasteful, as described previously. With the present invention, narrow zones of protection can be provided along both sides of the non-woven fabric while efficiently using much less of the trifluralin. The root barrier is typically required in only one direction. The non-woven fabric is used when water passing through in either or both directions is required. If permeability of air and water is not required, a solid plastic sheet (such as that described previously) with a barrier layer of EVOH or a nanoclay-containing compound will restrict movement of the trifluralin to one direction.

In accordance with this invention, a particularly desirable embodiment is the non-woven fabric of non-biodegradable polyolefin material. This type of material, known as a "geotextile" can be used with this invention for weed control, prevention of erosion on slopes, and other landscaping purposes. As mentioned previously, the polymer containing the root repellant dinitroaniline may be applied to the carrier sheet in various forms, e.g., as buttons or disks. The choice of the specific mode of distribution depends to a large part on the life desired for the root repellency.

The effectiveness of the invention in inhibiting root elongation is controlled by the soil concentration of dinitroaniline adjacent to the barrier. This is regulated by the release rate of the dinitroaniline from the disk-shaped elements into the sheet and from there into the soil. By inhibiting movement of the dinitroaniline directly into the soil, and forcing essentially all of the herbicide contained in the layered segments to move laterally through the carrier sheet, the invention enables use of various shapes and sizes of the segments, to utilize a reduced amount of herbicide. The barriers thereby reduce the rate of loss of herbicide from the layered segments, thereby reducing costs and/or extending the effective life of the product.

FIGS. 5 through 10 illustrate comparative uses of the invention. FIG. 5 illustrates a prior art weed control product 40, such as a prior art Biobarrier product. The herbicide-containing nodules 42 are distributed across the face of the sheet 44.

FIG. 6 shows a cross-section of the prior art product 40. The nodules 42 are structured similar to the nodules in FIG. 2. The dots marked "a" illustrate movement of the herbicide through the soil away from both sides of the sheet. The herbicide contained in the nodules will radiate outwardly directly into the soil as shown. The originally color of the sheet is white, but during use, the herbicide also migrates from the nodules into the sheet, and discolors the sheet, relatively uniformly, along both sides of the sheet.

FIG. 7 shows an alternate sheet material in which the prior art product of FIG. 6 has been altered by applying a barrier film 46 to the reverse side of the nodules 48 carried on the sheet 50. The barrier film is similar to that described previously. The dots "a" symbolize movement of the herbicide through the soil. The barrier layers 46 block dispersion of the herbicide into the soil on the reverse side of the carrier sheet, while the herbicide radiates outward from the nodules into the soil and also migrates through the sheet, and then into the soil.

FIG. 8 shows another alternate sheet material in which the prior art product of FIG. 6 has been altered by applying the barrier film 52 to the outwardly projecting curved surfaces of the nodules 54, on the front face of the carrier 56. The barrier is also applied to the portions of the nodules exposed to the reverse side of the sheet. The dots marked "a" symbolize movement of the herbicide through the soil, with the only movement on both sides being movement from the carrier sheet.

FIG. 9 illustrates one embodiment of the invention in which the layered segments 58 of herbicide-containing material according to the invention are applied to a front face of the carrier sheet 60. The carrier sheet comprises a non-porous plain plastic sheet comprising a polymeric material, such as polyolefin, which is capable of absorbing migrating herbicide from the layered segments. The barrier layers 62 are applied to the exposed surfaces of the layered segments, to provide a barrier between the segments and the soil. A second barrier layer 64 is applied to the entire reverse surface of the sheet 60. The dots "b" illustrate movement of the herbicide in a direction away from the front face of the carrier into the soil. The carrier sheet with its barrier layer on the reverse side has no herbicide moving out from the reverse side of the sheet. Movement of herbicide away from the individual layers of herbicide material is blocked by the barrier layers 62.

FIG. 10 shows an alternative form of the invention in which disk-shaped layered segments 66 are molded through the carrier sheet 68 and exposed to both sides of the carrier sheet. These disk-shaped layered segments are covered by separate barrier layers 70 applied to both sides of each disk. The dots marked "b" in FIG. 10 illustrate movement of the herbicide during use, in which the barrier layers block movement of the herbicide directly outwardly from the exposed surfaces of the layered segments. The herbicide is absorbed by the carrier sheet and the herbicide migrates outwardly from this sheet at a control release rate.

The FIG. 9 embodiment shows the most conservative use of the herbicide, followed by the embodiment of FIG. 10. The thickness of the larger, flat layered segments can have a nearly linear effect on the expected life of the patent. Use of the larger, flat segments makes it comparatively easier to apply the barrier layer—by rotogravure printing, for example.

For the layered segments formed as disks, spacing is generally on 1-inch to 3-inch centers, to produce a protective soil area. The dinitroaniline will slowly diffuse from the polymer with which it is mixed at a controlled rate. It will move through the sheet to be adsorbed to the soil adjacent to the barrier, and thus establish a zone in which the concentration is such as to prevent further elongation or penetration of the adjacent roots. As mentioned previously, the rate of diffusion from the button or disk into the sheet may be controlled by adding nanoclay to the composition of the button or disk as taught by U.S. Pat. No. 6,821,928 to Ruskin.

Some possible configurations using this invention, when compared with the Biobarrier prior art product, are shown below:

nanoclay reduces the release rate of the herbicide, such as trifluralin, at elevated temperatures, which can extend product expected life.

In another embodiment, the heat sensitivity problem can be reduced by providing a greater distribution of the layered segments on an upper section of the fabric, or by increasing the thickness of the layered segments in the areas of the fabric exposed to higher temperatures.

EXAMPLE

Two plastic containers with internal dimensions of 18.5"×18.5"×15" high, as illustrated in FIGS. 11 and 12 were set up as follows:

The containers were filled with potting soil.

80 shows the container: L×W×H: 18.5"×18.5"×15";

82 shows the heavy root growth;

84 shows a salix alba vitellina (golden willow) tree;

86 shows a drip irrigation line; and

Referring to FIG. 13, 87 shows a sheet of Biobarrier fabric 18.5" wide and 15" high, with nodules 88 on the right hand side. In the experiment, six rows of six nodules on the right hand side were removed, leaving 36 small holes in the non-woven fabric. Two such sheets were prepared.

| Biobarrier Nodule | | | As Improved Disk | | | | | |
|---|---|---|---|---|---|---|---|---|
| Diameter | 0.419 | inch | Diameter | 1.000 | 1.250 | 1.500 | inch | |
| Volume | 0.092 | cu inch | Thickness | 0.025 | 0.040 | 0.040 | inch | |
| Area | 0.152 | sq inch | Volume | 0.020 | 0.049 | 0.071 | cu inch | |
| Spacing center-to-center | 1.500 | inch | Area | 0.785 | 1.227 | 1.766 | sq. inch | |
| Ratio: | | | Spacing center-to-center | 2.082 | 2.332 | 2.582 | inch | |
| Pellet:space | 6.75% | | Ratio: | | | | | |
| Free Space | 93% | | Pellet:space | 18.12% | 22.56% | 26.50% | | |
| | | | Free Space | 82% | 77% | 73% | | |

Advantages of this invention are:

Longer life of the trifluralin and/or lower cost than the presently known Biobarrier product.

Less obnoxious blooming of trifluralin to the surface of the product.

Less environmental impact because less trifluralin is released per unit of time.

The dinitroanilines, in the concentrations released by the polymers, do not translocate into other parts of the plants. They do not kill plants beyond the seedling stage and do not injure them, except that growth may be restricted by the inhibition of new root production.

The present invention also addresses problems of temperature sensitivity with prior art weed control and root barrier products. With a barrier fabric placed vertically in a trench, the upper areas of the fabric being located nearer the surface can experience more heat buildup during use. The greater heat levels heat the trifluralin which boils off at the top more rapidly, thereby reducing expected product life.

Alternatively, a barrier fabric placed longitudinally in a shallow depth of soil, for weed control, can experience a heat sensitivity problem and reduced product life.

In one embodiment, the present invention addresses the heat sensitivity problem by incorporating a dispersed nanoclay into the carrier sheet fabric or material. The dispersed The Biobarrier sheet placed in one container had the remaining nodules on the left hand side of the sheet coated with an EVOH (ethyl-vinyl-alcohol) paint, as shown at 89 in FIG. 13.

The Biobarrier sheet placed in the second container was left as unchanged except for the removal of 36 nodules as described above.

A and B in FIG. 13 show specific holes through which roots intruded.

Both containers were identical except for the EVOH coating. The salix alba vitellina (golden willow) is a tree with very rapid and aggressive root growth. The trees grew for six months through the summer of 2010. The soil was then carefully removed. Root growth and root intrusion through the Biobarrier were observed. In both cases there was extremely aggressive root growth on the side where the tree was planted. In the case of the EVOH-treated Biobarrier, all the growth was contained behind the barrier except for one root coming through the hole in the Biobarrier marked B on the drawing. In the case of the untreated Biobarrier, a root was observed passing through the hole marked A, as well as massive growth under the Biobarrier on the side where the nodules had been removed. Note that B is much farther away from the nearest nodule than A.

The non-woven fabric is white and the trifluralin is orange, so one can observe the concentration of trifluralin by the intensity of the orange color. Trifluralin evaporates rapidly at elevated temperatures so one can expect that the fabric closest to the surface will be lighter in color than deeper down. Furthermore one could expect that the fabric furthest from the nearest nodule would be lighter. In the case of the uncoated nodules the fabric in the region on the right hand side was nearly white. In the case of the coated nodules the color difference on the same side, one inch below the surface, was not noticeable.

Both these observations confirm that by nearly eliminating direct movement of trifluralin out of the nodule into the soil, the lateral movement of the trifluralin from the nodules through the fabric has increased.

FIGS. 14-17 illustrate a co-extrusion process for forming the product of this invention. As illustrated in FIG. 14, a co-extruder forms the layered segments by simultaneously co-extruding the herbicide-containing material 90 and the resinous barrier material 92 as a stripe or a bead.

FIG. 15 illustrates the output of the co-extruder which includes multiple extruder die holes 94 which can co-extrude the stripes 96 in an oscillating pattern. The co-extruded pattern can vary as desired in either a continuous or a discontinuous pattern or bead. In the oscillating pattern, either the co-extruder die or the fabric support can be oscillated.

FIG. 16 shows a finished product 98 from the co-extruder of FIG. 15, in which the oscillating co-extrusions 96 are applied to a continuous sheet of porous geotextile fabric 100. The co-extruded material 90, 92 is squeezed into the fabric between rollers while hot and becomes embedded in the fabric.

FIG. 17 is a cross-sectional view of the finished product, showing the beads of herbicide-containing material 90 and their barrier layers 92 squeezed into the fabric 100.

FIGS. 18-21 illustrate a co-extrusion process for forming another embodiment of this invention. As illustrated in FIG. 18, a co-extruder forms the layered segments, by simultaneously co-extruding the herbicide-containing material 102 and the resinous barrier material 104 as a stripe or a bead. In this embodiment, the co-extrusion is applied to and bonded to a continuous non-porous carrier sheet. Since the layered segments are not absorbed into the depth of the sheet, the barrier layer 104 of the co-extrusion shown in FIG. 18 encompasses the entire exposed outer surface of the herbicide-containing component 102 of the co-extrusion.

FIG. 19 illustrates the output of the co-extruder which includes multiple extruder die holes 104 which co-extrude the stripes 106 in an oscillating pattern. The co-extruded pattern can vary in either a continuous or discontinuous pattern of stripes or beads.

FIG. 20 shows a finished product 108 from the co-extruder of FIG. 19, in which the co-extrusions 106 are applied to a surface of a continuous non-porous carrier sheet 108 such as a sheet of polyolefin material. The co-extrusions are laid on and bonded to the surface of the sheet 108.

FIG. 21 is a cross-sectional view of the finished product, showing the beads of herbicide-containing material 102 and their barrier layers 104 adhered to the surface of the sheet. The sheet can be in multi-layer form, with a bottom layer 110 forming a barrier to the movement of the herbicide to one side of the sheet. Alternatively, the barrier layer 110 can be a continuous coating of a barrier paint.

What is claimed is:

1. A sheet material for preventing entry of unwanted roots into a volume of soil, comprising a flexible carrier sheet of a non-biodegradable polymeric herbicide-absorbing material; discrete spaced-apart layered segments of a polymer containing a dinitroaniline herbicide positioned on an outer surface of the carrier sheet, leaving an uncoated exposed surface of the carrier sheet in between the spaced-apart layered segments, the layered segments comprising a composition effective to retain and control the release rate of said herbicide; the layered segments having outer surfaces coated with a layer of barrier material so that the layered segments block diffusion of the herbicide directly through said barrier material, to cause essentially all of the herbicide contained in the layered segments to be distributed away from the layered segments and laterally through the herbicide-absorbing carrier sheet, for ultimately dispersing the herbicide away from the uncoated exposed outer surface of the carrier sheet and into the soil at a controlled release rate.

2. The sheet material as defined in claim 1, in which the herbicide is absorbed in carbon black, the concentration of the dinitroaniline herbicide in said layered segments being from about 2 wt. % to about 30 wt. %, based on the solids contained in the layered segments, the carbon black effective to retain and control the release rate of the herbicide.

3. The sheet material as defined in claim 1, wherein said polymer contained in the layered segments is selected from the group consisting of polyethylenes, polypropylenes, copolymers and mixtures of polyethylenes and polypropylenes, polyvinylacetate, poly(ethylene vinyl acetate), poly(ethyleneacrylic acid), poly(ethylene ethyl acrylate), polybutylene.

4. The sheet material as defined in claim 1, wherein said dinitroaniline herbicide is selected from the group consisting of trifluralin, benfluralin, isopropalin, oryzalin, ethalfluralin, pendimethalin, and profluralin.

5. The sheet material as defined in claim 1, wherein the carrier sheet material is selected from the group consisting of polyethylenes, polypropylenes, copolymers and mixtures of polyethylenes and polypropylenes, polyvinylacetate, poly(ethylene vinyl acetate), poly(ethyleneacrylic acid), poly(ethylene ethyl acrylate), polybutylene.

6. The sheet material as defined in claim 1, wherein said carrier sheet is one of (a) to (c): (a) a fabric which is porous to water; (b) a non-woven fabric of a non-biodegradable thermoplastic polyolefin material; or (c) a continuous non-porous sheet of a non-biodegradable polyolefin material.

7. The sheet material as defined in claim 1, wherein said layered segments are thin, flat disk-shaped elements having a width greater than their thickness, in which the layered segments are from about ¼ to about 1 inch in diameter and from about 1/40 inch minimum to about 3/8 inch maximum in thickness, and in which said layered segments are spaced apart by an average of about 1 to about 3 inches.

8. The sheet material as defined in claim 1, in which the layered segments and the barrier layers comprise a co-extrusion applied to, bonded to, or embedded in the carrier sheet, and in which the layered segments are continuous or discontinuous beads of said herbicide-containing material.

9. The sheet material as defined in claim 1 in which the rate of diffusion of the herbicide from said layered segments into the carrier sheet material is controlled by a dispersed nano-clay incorporated into the composition of said layered segments.

10. The sheet material as defined in claim 9 in which the barrier layer material comprises a paint film binder or lacquer selected from the group consisting of EVOH, vinyl, polyolefin, polyurethane and acrylic.

11. The material as defined in claim 1, wherein said carrier sheet comprises a non-woven carrier sheet comprising a multilayer extrusion with at least one layer containing EVOH, or wherein said carrier sheet comprises a continuous non-porous polyolefin sheet comprising a multilayer extrusion with at least one layer containing EVOH, or one layer containing a nanoclay, or one layer comprising a paint coat.

12. The material as defined in claim 1, wherein said barrier material comprises a thin film or layer or coating of a polymeric material which may optionally contain a dispersed nanoclay.

13. The sheet material as defined in claim 1 in which the barrier layer material comprises a paint film binder or lacquer selected from the group consisting of EVOH, vinyl, polyolefin, polyurethane and acrylic.

14. A combination of a zone of protection and a controlled release barrier, the combination comprising a zone of protection which includes a volume of soil from which unwanted root growth is excluded; and a sheet material positioned in the soil for providing a controlled release barrier that prevents entry of unwanted roots into the volume of soil, the sheet material comprising a flexible porous carrier sheet of a non-biodegradable herbicide-absorbing thermoplastic polyolefin material; discrete spaced-apart layered segments of a polyolefin material containing a herbicidal dinitroaniline positioned on an outer surface of the carrier sheet, leaving an uncoated exposed surface of the carrier sheet in between the spaced-apart layered segments, the layered segments comprising a composition effective to retain and control the release rate of said herbicide; the layered segments having outer surfaces coated with a layer of barrier material so that the layered segments block diffusion of the dinitroaniline directly into the soil through said barrier material, such that, when said carrier sheet is buried in the soil, essentially all of said dinitroaniline is distributed away from the layered segments and laterally through the herbicide-absorbing carrier sheet, for ultimately dispersing the dinitroaniline away from the uncoated exposed outer surface of the carrier sheet and into the adjacent soil, to form said zone of protection along the buried sheet material; the dinitroaniline dispersed at such a release rate, and over such a period of time, as to exclude roots over a period of years without killing plants beyond the seedling stage.

15. The combination defined in claim 14, wherein said layered segments are spaced apart disk-shaped elements, or continuous or discontinuous extrusions which have been applied to, bonded to, or embedded in the carrier sheet.

16. The combination defined in claim 14, wherein said layered segments have a width greater than their thickness and wherein the volume-to-area ratio of the layered segments is less than 0.10 inch.

17. The combination defined in claim 14, in which a nanoclay is incorporated into the composition of the layered segments, and in which a nanoclay is dispersed in either the barrier layer material, or the carrier sheet material, or both.

18. The combination defined in claim 14, wherein said layered segments are thin, flat disk-shaped elements having a width greater than their thickness, in which the layered segments are from about ¼ to about 1 inch in diameter and from about 1/40 inch minimum to about 3/8 inch maximum in thickness, and in which said layered segments are spaced apart by an average of about 1 to about 3 inches.

19. The combination defined in claim 14 in which the barrier layer material comprises a paint film binder or lacquer selected from the group consisting of EVOH, vinyl, polyolefin, polyurethane and acrylic.

20. The combination defined in claim 14, in which the zone of protection is located in a septic drain-field or a waste burial site.

21. A method for creating a herbicidal zone of protection in a volume of soil to protect against unwanted root growth in the zone of protection, the method comprising:
positioning a herbicidal root growth barrier in the soil;
the root growth barrier comprising a sheet material for preventing entry of unwanted roots into the volume of soil, comprising a flexible carrier sheet of a non-biodegradable polymeric herbicide-absorbing material; discrete spaced-apart layered segments of a polymer containing a dinitroaniline herbicide positioned on an outer surface of the carrier sheet, leaving an uncoated exposed surface of the carrier sheet in between the spaced-apart layered segments, the layered segments comprising a composition effective to retain and control the release rate of said herbicide; the layered segments having outer surfaces coated with a layer of barrier material so that the layered segments block diffusion of the herbicide directly through said barrier material into the soil;
the barrier layers causing essentially all of the herbicide contained in the layered segments to be distributed away from the layered segments and laterally through the herbicide-absorbing carrier sheet for ultimately dispersing the herbicide away from the uncoated exposed outer surface of the carrier sheet and into the soil to exclude root growth and thereby form said zone of protection along the buried sheet material.

22. The method defined in claim 21, in which the barrier material comprises a paint film binder or lacquer selected from the group consisting of EVOH, vinyl, polyolefin, polyurethane and acrylic.

23. The method defined in claim 21, wherein said carrier sheet is one of (a) to (c): (a) a fabric which is porous to water; (b) a non-woven fabric of a non-biodegradable thermoplastic polyolefin material; or (c) a continuous non-porous sheet of a non-biodegradable polyolefin material.

* * * * *